United States Patent [19]
Gers-Barlag

[11] Patent Number: 5,851,542
[45] Date of Patent: Dec. 22, 1998

[54] COSMETIC AND DERMATOLOGICAL LIGHT PROTECTION FORMULATIONS HAVING A CONTENT OF TRIAZINE DERIVATIVES AND GLYCEROL MONO- OR DICARBOXYLIC ACID MONOESTERS

[75] Inventor: Heinrich Gers-Barlag, Kummerfeld, Germany

[73] Assignee: Beiersdorf AG, Hamburg, Germany

[21] Appl. No.: 910,186

[22] Filed: Aug. 13, 1997

[30] Foreign Application Priority Data

Aug. 16, 1996 [DE] Germany .................. 196 32 913.2

[51] Int. Cl.⁶ ........................................ A61K 6/00
[52] U.S. Cl. ................ 424/401; 424/59; 424/61; 424/69; 424/78.02; 424/78.03
[58] Field of Search .................. 424/61, 59, 69, 424/78.02, 78.03, 401

[56] References Cited

U.S. PATENT DOCUMENTS

5,256,717  10/1993  Stauffer et al. .................. 524/293

*Primary Examiner*—Terressa Mosley
*Attorney, Agent, or Firm*—Sprung Kramer Schaefer & Briscoe

[57] ABSTRACT

Active compound combinations of
(a) tris(2-ethylhexyl) 4,4',4"-(1,3,5-triazine-2,4,6-triyltriimino)trisbenzoate and
(b) glycerol mono- or dicarboxylic acid monoesters which have a light-protection action.

10 Claims, No Drawings

COSMETIC AND DERMATOLOGICAL LIGHT PROTECTION FORMULATIONS HAVING A CONTENT OF TRIAZINE DERIVATIVES AND GLYCEROL MONO- OR DICARBOXYLIC ACID MONOESTERS

DESCRIPTION

The present invention relates to cosmetic and dermatological light protection formulations, in particular skin-care cosmetic and dermatological light protection formulations.

The damaging effect of the ultraviolet part of solar radiation on the skin is generally known. While rays having a wavelength below 290 nm (the so-called UVC range) are absorbed by the ozone layer in the earth's atmosphere, rays in the range between 290 nm and 320 nm, the so-called UVB range, cause erythema, simple sunburn or even burns of greater or lesser severity.

The narrower range around 308 nm is stated as the maximum for the erythema activity of sunlight.

Numerous compounds, which are usually derivatives of 3-benzylidenecamphor, of 4-aminobenzoic acid, of cinnamic acid, of salicylic acid, of benzophenone or also of 2-phenylbenzimidazole, are known for protection against UVB radiation.

It is also important to have available filter substances for the range between about 320 nm and about 400 nm, the so-called UVA range, since rays in this range can also cause damage. It has thus been proved that UVA radiation leads to damage to the elastic and collagenic fibres of connective tissue, which causes the skin to age prematurely, and that it is to be regarded as a cause of numerous phototoxic and photoallergic reactions. The damaging influence of UVB radiation may be intensified by UVA radiation.

However, UVA radiation can also lead to photochemical reactions, the photochemical reaction products then intervening in skin metabolism.

Such photochemical reaction products are chiefly free-radical compounds, for example hydroxyl radicals. Undefined free-radical photoproducts which are formed in the skin itself can also show uncontrolled secondary reactions because of their high reactivity. However, singlet oxygen, a non-radical excited state of the oxygen molecule, may also occur under UV irradiation, as may short-lived epoxides and many others. Singlet oxygen, for example, is distinguished from the triplet oxygen normally present (free-radical ground state) by an increased reactivity. Nevertheless, excited, reactive (free-radical) triplet states of the oxygen molecule also exist.

UV radiation is furthermore counted among ionizing radiation. There is therefore the risk of ionic species also being formed during UV exposure, which then in turn are capable of intervening oxidatively in biochemical processes.

An advantageous UVB filter is tris(2-ethylhexyl) 4,4',4"-(1,3,5-triazine-2,4,6-triyltriimino)-trisbenzoate, synonym: 2,4,6-tris-[anilino(p-carbo-2'-ethyl-1'-hexyloxy)]-1,3,5-triazine.

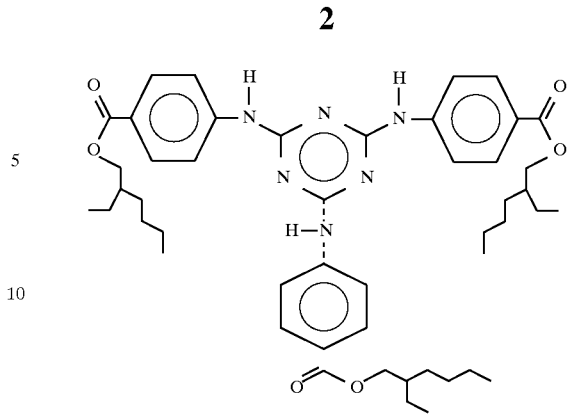

This UVB filter substance is marketed by BASF Aktiengesellschaft under the trade name UVINUL® T 150, and is distinguished by good UV-absorbing properties.

The main disadvantage of this UVB filter is its poor solubility in lipids. Known solvents for this UVB filter can dissolve a maximum of about 15% by weight of this filter, corresponding to about 1–1.5 by weight of dissolved, and therefore active, UV filter substance.

It was therefore surprising and unforeseeable to the expert that active compound combinations of
(a) tris(2-ethylhexyl) 4,4',4"-(1,3,5-triazine-2,4,6-triyltriimino)trisbenzoate and
(b) one or more surface-active substances chosen from the group consisting of glycerol mono- and dicarboxylic acid monoesters of the general formula

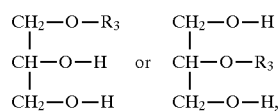

wherein $R_3$ is a branched or unbranched acyl radical having 6–24 carbon atoms,
which have a light protection action, and remedy the disadvantages of the prior art.

The invention also particularly relates to the use of one or more surface-active substances chosen from the group consisting of glycerol mono- and dicarboxylic acid monoesters of the general formula

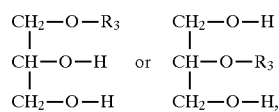

wherein $R_3$ is a branched or unbranched acyl radical having 6–24 carbon atoms, as solvent, solubilizing agent or a solubilizer for tris(2-ethylhexyl) 4,4',4"-(1,3,5-triazine-2,4,6-triyltriimino)trisbenzoate, in particular for use in light protection compositions.

According to the invention, it is possible to double the amounts of tris(2-ethylhexyl) 4,4',4"-( 1,3,5-triazine-2,4,6-triyltriimino)trisbenzoate employed in cosmetic or dermatological formulations compared with the prior art.

It was astonishing that, by addition of surface-active glycerol mono- or dicarboxylic acid monoesters used according to the invention, stabilization of solutions of tris(2-ethylhexyl) 4,4',4"- (1,3,5-triazine-2,4,6-triyltriimino) trisbenzoate is effected, since the latter substance not only has a poor solubility but also readily recrystallizes from its solution. The invention therefore also relates to a method of stabilizing solutions of tris(2-ethylhexyl) 4,4',4"-(1,3,5-triazine-2,4,6-triyltriimino)trisbenzoate, characterized in that an active content of glycerol mono- or dicarboxylic acid monoesters used according to the invention is added to such solutions.

R₃ is preferably a myristyl radical, palmityl radical, stearyl radical or eicosyl radical.

As surface-active substances listed under point (b), glyceryl stearate, which is commercially obtainable, for example, under the trade name Tegin® M from the company Th. Goldschmidt KG, has proved to be particularly advantageous in the context of the present invention.

The total amount of tris(2-ethylhexyl) 4,4',4"-(1,3,5-triazine-2,4,6-triyltriimino)trisbenzoate in the finished cosmetic or dermatological formulations is advantageously chosen from the range of 0.1–10.0% by weight, preferably 0.5–6.0 by weight, based on the total weight of the formulations.

The total amount of one or more surface-active glycerol mono- or dicarboxylic acid monoesters used according to the invention in the finished cosmetic or dermatological formulations is advantageously chosen from the range of 0.1–25% by weight, preferably 0.5–15.0% by weight, based on the total weight of the formulations.

It is advantageous to choose weight ratios of tris(2-ethylhexyl) 4,4',4"-(1,3,5-triazine-2,4,6-triyltriimino) trisbenzoate and one or more glycerol mono- or dicarboxylic acid monoesters used according to the invention from the range from 1:10 to 10:1, preferably 1:4 to 4:1.

Cosmetic and dermatological formulations according to the invention advantageously furthermore comprise inorganic pigments based on metal oxides and/or other metal compounds which are sparingly soluble or insoluble in water, in particular the oxides of titanium (TiO₂), zinc (ZnO), iron (for example Fe₂O₃), zirconium (ZrO₂), silicon (SiO₂), manganese (for example MnO), aluminium (Al₂O₃) and cerium (for example Ce₂O₃), mixed oxides of the corresponding metals and mixtures of such oxides. The pigments are particularly preferably pigments based on TiO₂.

It is particularly advantageous in the context of the present invention, although not necessary, for the inorganic pigments to be present in hydrophobic form, i.e. to be treated with a water-repellent treatment on the surface. This surface treatment can comprise providing the pigments with a thin hydrophobic layer by processes known per se.

Such a process comprises, for example, producing the hydrophobic surface layer by a reaction in accordance with

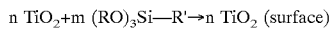

n and m here are stoichiometric parameters which are to be employed as desired, and R and R' are the desired organic radicals. Hydrophobicized pigments prepared analogously to DE-A 33 14 742 are advantageous.

Advantageous TiO₂ pigments are obtainable, for example, under the trade name MT 100 T from TAYCA, and furthermore M 160 from Kemira and T 805 from Degussa.

The cosmetic and/or dermatological light protection formulations according to the invention can have the customary composition and can be used for cosmetic and/or dermatological light protection, and furthermore for treatment, care and cleansing of the skin and/or hair and as a make-up product in decorative cosmetics.

For use, the cosmetic and dermatological formulations according to the invention are applied to the skin and/or hair in an adequate amount in the manner customary for cosmetics.

Those cosmetic and dermatological formulations which are in the form of a sunscreen composition are particularly preferred. These can advantageously additionally comprise at least one further UVA filter and/or at least one further UVB filter and/or at least one inorganic pigment, preferably an inorganic micropigment.

The cosmetic and dermatological formulations according to the invention can comprise cosmetic auxiliaries such as are usually used in such formulations, for example preservatives, bactericides, perfumes, substances for preventing foaming, dyestuffs, pigments which have a colouring action, thickeners, humidifying and/or humectant substances, fats, oils, waxes or other customary constituents of a cosmetic or dermatological formulation, such as alcohols, polyols, polymers, foam stabilizers, electrolytes, organic solvents or silicone derivatives.

An additional content of antioxidant is in general preferred. Favourable antioxidants which can be used according to the invention are all the antioxidants which are suitable or customary for cosmetic and/or dermatological applications.

The antioxidants are advantageously chosen from the group consisting of amino acids (for example glycine, histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, chlorogenic acid and derivatives thereof, liponic acid and derivatives thereof (for example dihydroliponic acid), aurothioglucose, propylthiouracil and other thiols (for example thioredoxin, glutathione, cysteine, cystine, cystamine and the glucosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to μmol/kg), and furthermore (metal) chelators, (for example α-hydroxy-fatty acids, palmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, furfurylidenesorbitol and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, ZnSO₄), selenium and derivatives thereof (for example selenium-methionine), stilbenes and derivatives thereof (for example stilbene oxide and trans-stilbene oxide) and the derivatives of these active compounds mentioned which are suitable according to the invention (salts, esters, ethers, sugars, nucelotides, nucleosides, peptides and lipids).

The amount of the abovementioned antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range from 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

The lipid phase can advantageously be chosen from the following group of substances:

mineral oils and mineral waxes;

oils, such as triglycerides of capric or of caprylic acid, but preferably castor oil;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

alkyl benzoates;

silicone oils, such as dimethylpolysiloxanes, diethylpolysiloxanes, diphenylpolysiloxanes and mixed forms thereof.

The oily phase of the emulsions, oleogels or hydrodispersions or lipodispersions in the context of the present invention is advantageously chosen from the group consisting of esters of saturated and/or unsaturated, branched and/or unbranched alkane carboxylic acids having a chain length of 3 to 30 C atoms and saturated and/or unsaturated, branched and/or unbranched alcohols having a chain length of 3 to 30 C atoms, or from the group consisting of esters of aromatic carboxylic acids and saturated and/or unsaturated, branched and/or unbranched alcohols having a chain length of 3 to 30 C atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate and erucyl erucate and synthetic, semi-synthetic and naturally occurring mixtures of such esters, for example jojoba oil.

The oily phase can furthermore advantageously be chosen from the group consisting of branched and unbranched hydrocarbons and waxes, silicone oils, dialkyl ethers, the group consisting of saturated or unsaturated, branched or unbranched alcohols and fatty acid triglycerides, in particular the triglycerol esters of saturated and/or unsaturated, branched and/or unbranched alkanecarboxylic acids having a chain length of 8 to 24, in particular 12–18 C atoms. The fatty acid triglycerides can advantageously be chosen, for example, from the group consisting of synthetic, semi-synthetic and naturally occurring oils, for example olive oil, sunflower oil, soya oil, groundnut oil, rapeseed oil, almond oil, palm oil, coconut oil, palm kernel oil and many others.

Any desired mixtures of such oil and wax components can advantageously be employed in the context of the present invention. If appropriate, it may also be advantageous to employ waxes, for example cetyl palmitate, as the sole lipid component of the oily phase.

The oily phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate, and isotridecyl isononanoate are particularly advantageous.

Of the hydrocarbons, paraffin oil, squalane and squalene are advantageously to be used in the context of the present invention.

The oily phase can furthermore advantageously have a content of cyclic or linear silicone oils or consist entirely of such oils, although it is preferable to use an additional content of other oily phase components, in addition to the silicone oil or the silicone oils.

Cyclomethicone (octamethylcyclotetrasiloxane) is advantageously employed as the silicone oil to be used according to the invention. However, other silicone oils are also advantageously to be used in the context of the present invention, for example, hexamethylcycliotrisiloxane, polydimethylsiloxane and poly(methylphenylsiloxane).

Mixtures of cyclomethicone and isotridecyl isononanoate, and of cyclomethicone and 2-ethylhexyl isostearate are furthermore particularly advantageous.

The aqueous phase of the formulations according to the invention advantageously comprises, if appropriate, alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, for example ethanol, isopropanol, 1,2-propanediol and glycerol and, in particular, one or more thickeners, which can advantageously be chosen from the group consisting of silicon dioxide, aluminium silicates, polysaccharides and derivatives thereof, for example hyaluronic acid, xanthan gum and hydroxypropyl-methylcellulose, particularly advantageously from the group consisting of polyacrylates, preferably a polyacrylate from the group consisting of so-called Carbopols, for example Carbopols of types 980, 981, 1382, 2984 and 5984, in each case individually or in combination.

The cosmetic or dermatological light protection formulations advantageously comprise inorganic pigments, in particular micropigments, for example in amounts of 0.1% by weight to 30% by weight, preferably in amounts of 0.5% by weight to 10% by weight, but in particular 1% by weight to 6% by weight, based on the total weight of the formulations.

It is advantageous according to the invention to employ oil-soluble UVA filters and/or UVB filters in the lipid phase and/or water-soluble UVA filters and/or UVB filters in the aqueous phase, in addition to the combinations according to the invention.

The light protection formulations according to the invention can advantageously comprise further substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic formulations which protect the skin from the entire range of ultraviolet radiation. They can also be used as sunscreen compositions.

The further UVB filters can be oil-soluble or water-soluble. Advantageous oil-soluble UVB filter substances are, for example:

- 3-benzylidenecamphor derivatives, preferably 3-(4-methylbenzylidene)camphor and 3-benzylidene-camphor;
- 4-aminobenzoic acid derivatives, preferably 2-ethylhexyl 4-(dimethylamino)benzoate and amyl 4-(dimethylamino)benzoate;
- esters of cinnamic acid, preferably 2-ethylhexyl 4-methoxycinnamate and isopentyl 4-methoxycinnamate,
- derivatives of benzophenone, preferably 2-hydroxy-4-methoxybenzophenone, 2-hydroxy-4-methoxy-4'-methylbenzophenone and 2,2'-dihydroxy-4-methoxybenzophenone;
- esters of benzalmalonic acid, preferably di(2-ethylhexyl) 4-methoxybenzalmalonate.

Advantageous water-soluble UVB filter substances are, for example:

- salts of 2-phenylbenzimidazole-5-sulphonic acid, such as its sodium, potassium or its triethanolammonium salt, and the sulphonic acid itself;
- sulphonic acid derivatives of benzophenones, preferably 2-hydroxy-4-methoxybenzophenone-5-sulphonic acid and salts thereof;
- sulphonic acid derivatives of 3-benzylidene-camphor, such as, for example, 4-(2-oxo-3-bornylidenemethyl) benzenesulphonic acid, 2-methyl-5-(2-oxo-3-bornylidenemethyl)-benzenesulphonic acid and salts thereof.

The list of further UVB filters mentioned, which can be used in combination with the active compound combinations according to the invention, is of course not intended to be limiting.

It may also be advantageous to combine the combinations according to the invention with further UVA filters which have usually been contained to date in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations and to formulations which comprise these combinations. The amounts used for the UVB combination can be employed.

It is furthermore advantageous to combine the active compound combinations according to the invention with further UVA and/or UVB filters.

It is also particularly advantageous to combine the active compound combinations according to the invention with salicyclic acid derivatives, some representatives of which are known and which likewise can absorb UV radiation. Customary UV filters include

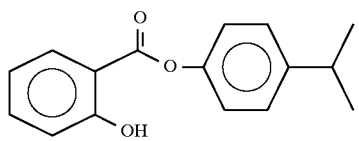

(4-isopropylbenzyl salicylate)

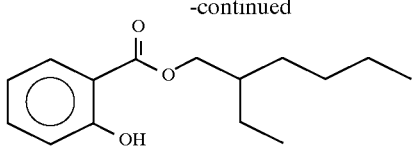

(2-ethylhexyl salicylate, octyl salicylate)

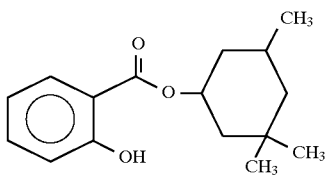

(homoethyl salicylate)

The invention also relates to a process for the preparation of the cosmetic and/or dermatological light protection formulations according to the invention, which is characterized in that tris(2-ethylhexyl) 4,4',4"-(1,3,5-triazine-2,4,6-triyltriimino)trisbenzoate is suspended and, if desired, homogenized in one or more surface-active glucose derivatives used according to the invention or an oily phase having a content of surface-active glucose derivatives used according to the invention, with uniform stirring and if appropriate with heating, the mixture is combined with further lipid components, if appropriate, and with one or emuslifiers, if appropriate, thereafter, the oily phase is mixed with the aqueous phase, into which a thickener has been incorporated, if appropriate, and which preferably has about the same temperature as the oily phase, the components are homogenized, if desired, and the mixture is allowed to cool to room temperature. After cooling to room temperature, homogenziation can be carried out again, especially if volatile constituents are still to be incorporated.

The following examples are intended to illustrate the present invention, without limiting it. Unless stated otherwise, all the amounts, contents and percentage contents are based on the weight and the total amount or on the total weight of the formulations.

EXAMPLE 1

|  | % by weight |
|---|---|
| Glyceryl stearate SE | 3 50 |
| Sorbitan monostearate | 1.80 |
| Glycerol | 3.00 |
| Cetearyl alcohol | 0.50 |
| Octyldodecanol | 7.00 |
| Caprylyl ether | 8.00 |
| Uvinul T150 | 3.00 |
| Cetearyl isononanoate | 6.00 |
| Carbomer | 0.20 |
| Preservative | q.s. |
| Perfume | q.s. |
| Water, demineralized | to 100.00 |

EXAMPLE 2

|  | % by weight |
|---|---|
| Glyceryl stearate | 2.50 |
| Sorbitan monostearate | 3.50 |
| Glycerol | 3.00 |

-continued

| | % by weight |
|---|---|
| Cetearyl alcohol | 1.50 |
| Sodium hydroxide (45% strength) | 0.13 |
| Octyldodecanol | 7.00 |
| Capric/caprylic triglyceride | 5.00 |
| Cetearyl isononanoate | 6.00 |
| Uvinul T150 | 5.00 |
| Carbomer | 0.20 |
| Preservative | q.s. |
| Perfume | q.s. |
| Water, demineralized | to 100.00 |

EXAMPLE 3

| | % by weight |
|---|---|
| Sorbitan monostearate | 3.50 |
| Butylene glycol | 3.50 |
| Cetearyl alcohol | 3.00 |
| Xanthan gum | 0.35 |
| $C_{12}$–$C_{15}$ Alkyl benzoate | 10.0 |
| Uvinul T150 | 4.00 |
| Cetearyl isononanoate | 6.00 |
| Preservative | q.s. |
| Perfume | q.s. |
| Water, demineralized | to 100.00 |

EXAMPLE 4

| | % by weight |
|---|---|
| Glyceryl stearate SE | 3.50 |
| Sorbitan monostearate | 1.80 |
| Glycerol | 3.00 |
| Cetearyl alcohol | 0.50 |
| Octyl dodecanol | 7.00 |
| Caprylyl ether | 8.00 |
| Uvinul T150 | 3.00 |
| Parsol 1789 | 2.00 |
| Eusolex 6300 | 1.00 |
| Titanium dioxide | 2.00 |
| Cetearyl isononanoate | 6.00 |
| Carbomer | 0.20 |
| Preservative | q.s. |
| Perfume | q.s. |
| Water, demineralized | to 100.00 |

EXAMPLE 5

| | % by weight |
|---|---|
| Glyceryl stearate | 2.50 |
| Sorbitan monostearate | 3.50 |
| Glycerol | 3.00 |
| Cetearyl alcohol | 1.50 |
| Sodium hydroxide (45% strength) | 0.13 |
| Octyldodecanol | 7.00 |
| Capric/caprylic triglyceride | 5.00 |
| Cetearyl isononanoate | 6.00 |
| Uvinul T150 | 5.00 |
| Parsol 1789 | 2.00 |
| Eusolex 6300 | 1.00 |
| Titanium dioxide | 2.00 |
| Carbomer | 0.20 |
| Preservative | q.s. |
| Perfume | q.s. |
| Water, demineralized | to 100.00 |

EXAMPLE 6

| | % by weight |
|---|---|
| Sorbitan monostearate | 3.50 |
| Butylene glycol | 5.00 |
| Cetearyl alcohol | 3.00 |
| Xanthan gum | 0.35 |
| $C_{12}$–$C_{15}$ Alkyl benzoate | 10.00 |
| Uvinul T150 | 4.00 |
| Parsol 1789 | 2.00 |
| Eusolex 6300 | 1.00 |
| Titanium dioxide | 2.00 |
| Cetearyl isononanoate | 6.00 |
| Preservative | q.s. |
| Perfume | q.s. |
| Water, demineralized | to 100.00 |

I claim:

1. A cosmetic or dermatologic formulation for protecting skin against the damaging effects of UV light, said formulation comprising an effective amount therefor of a combination of:

(a) tris(2-ethylhexyl) 4,4',4"-(1,3,5-triazine-2,4,6-triyltriimino) trisbenzoate and (b) one or more surface-active substances selected from the group consisting of glycerol mono- and dicarboxylic acid monoesters of the general formula

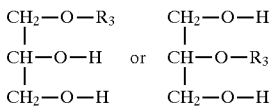

wherein $R_3$ is a branched or unbranched acyl radical having 6–24 carbon atoms.

2. A cosmetic or dermatologic formulation according to claim 1, wherein the total amount of tris(2-ethylhexyl) 4,4',4"-(1,3,5-triazine-2,4,6-triyltriimino) trisbenzoate in the cosmetic or dermatologic formulation is in the range of 0.1–10.0% by weight, based on the total weight of the formulation.

3. A cosmetic or dermatologic formulation according to claim 1, wherein the total amount of glycerol mono- or dicarboxylic acid monoesters in the cosmetic or dermatologic formulation is in the range of 0.1–25.0% by weight, based on total weight of the formulation.

4. A cosmetic or dermatologic formulation according to claim 2, wherein the total amount of tris(2-ethylhexyl) 4,4',4"-(1,3,5-triazine-2,4,6-triyltriimino)trisbenzoate in the cosmetic or dermatologic formulation is in the range of 0.5–6.0% by weight based on the total weight of the formulation.

5. A cosmetic or dermatologic formulation according to claim 3, wherein the total amount of glycerol mono- or dicarboxylic acid monoesters in the cosmetic or dermatologic formulation is in the range of 0.5–15.0% by weight based on the total weight of the formulation.

6. A method of protecting skin from the damaging effects of UV light comprising applying to said skin an effective amount therefor of a cosmetic or dermatologic composition comprising a skin protective effective amount of a combination of:

(a) tris(2-ethylhexyl) 4,4',4"-(1,3,5-triazine-2,4,6-triyltriimino)trisbenzoate; and (b) one or more surface-active substances selected from the group consisting of glycerol mono- and dicarboxylic acid monoesters of the formula

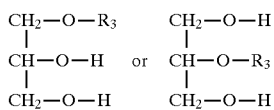

wherein $R_3$ is a branched or unbranched acyl radical having 6–24 carbon atoms.

7. The method according to claim 6, wherein the total amount of tris(2-ethylhexyl) 4,4',4"-(1,3,5-triazine-2,4,6-triyltriimino)trisbenzoate in the cosmetic or dermatologic formulation is in the range of 0.1–10.0% by weight based on the total weight of the formulation.

8. The method according to claim 7, wherein the total amount of tris(2-ethylhexyl) 4,4',4"-(1,3,5-triazine-2,4,6-triyltriimino)trisbenzoate in the cosmetic or dermatologic formulation is in the range of 0.5–6.0% by weight based on the total weight of the formulation.

9. The method according to claim 6, wherein the total amount of glycerol mono- or dicarboxylic acid monoesters in the cosmetic or dermatologic formulations is in the range of 0.1–25.0% by weight based on the total weight of the formulation.

10. The method according to claim 9, wherein the total amount of glycerol mono- or dicarboxylic acid monoesters in the cosmetic or dermatological formulation is in the range of 0.5–15.0% by weight based on the total weight of the formulation.

* * * * *